United States Patent
Schneiderman

(10) Patent No.: US 6,547,795 B2
(45) Date of Patent: Apr. 15, 2003

(54) SURGICAL GUIDE SYSTEM FOR STABILIZATION OF THE SPINE

(75) Inventor: Gary Andrew Schneiderman, Sacramento, CA (US)

(73) Assignee: DePuy AcroMed, Inc., Raynaham, MA (US)

(*) Notice: Subject to any disclaimer, the term of this patent is extended or adjusted under 35 U.S.C. 154(b) by 0 days.

(21) Appl. No.: 09/929,292

(22) Filed: Aug. 13, 2001

(65) Prior Publication Data

US 2003/0032965 A1 Feb. 13, 2003

(51) Int. Cl.$^7$ .................................................. A61F 2/00
(52) U.S. Cl. .......................................... 606/96; 606/102
(58) Field of Search ........................... 606/96, 102, 61, 606/97, 98

(56) References Cited

U.S. PATENT DOCUMENTS

| 4,883,048 A | * | 11/1989 | Purnell et al. | |
| 4,907,577 A | * | 3/1990 | Wu | 606/87 |
| 4,985,032 A | * | 1/1991 | Goble | 606/96 |
| 5,152,764 A | * | 10/1992 | Goble | 606/96 |
| 5,269,786 A | * | 12/1993 | Morgan | 606/96 |
| 5,423,826 A | * | 6/1995 | Coates et al. | 606/96 |
| 5,704,937 A | * | 1/1998 | Martin | 606/61 |
| 6,287,313 B1 | | 9/2001 | Sasso | |
| 6,340,363 B1 | * | 1/2002 | Bolger et al. | 606/90 |
| 6,342,056 B1 | * | 1/2002 | Mac-Thiong et al. | 606/96 |

OTHER PUBLICATIONS

F. P. Magerl, M.D., "Stabilization of the Lower Thoracic and Lumbar Spine with External Skeletal Fixation", *Clinical Orthopaedics and Related Research* (1984)189: 125–141.
H. H. Boucher, "A Method of Spinal Fusion", *The Journal of Bone and Joint Surgery* (1959) 41B(2): 248–259.
M. E. Muller, et al., "Manual of Internal Fixation", $3^{rd}$ ed. (1991): 186–203.

* cited by examiner

*Primary Examiner*—Ralph A. Lewis
(74) *Attorney, Agent, or Firm*—Nutter McClennen & Fish LLP

(57) ABSTRACT

A system of instruments and a method for using these instruments for effective spinal stabilization using cannulated bone screws is described. In particular, the system and method provides accurate and efficient measurement of the appropriate screw length to be inserted in a patient with a lower spine injury. The system and method further enables accurate orientation or placement of the cannulated bone screws from outside the patient's body. The present method describes a surgical technique for the placement of cannulated bone screw for translaminar facet, transfacet, and general orthopedic applications.

26 Claims, 13 Drawing Sheets

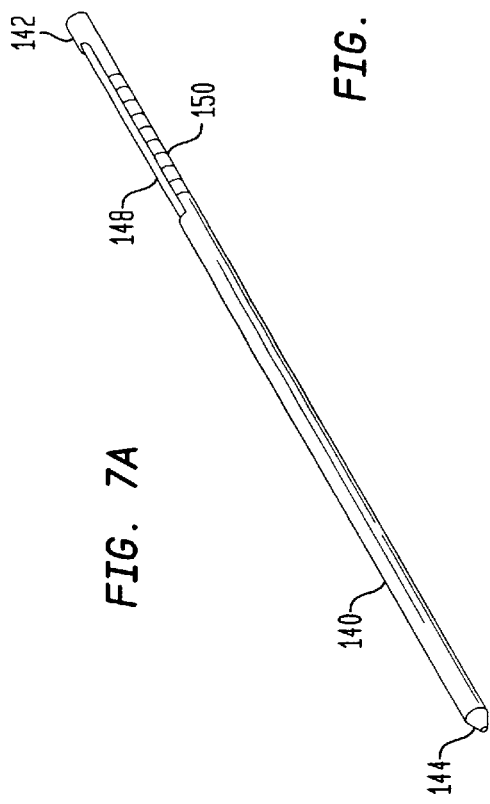
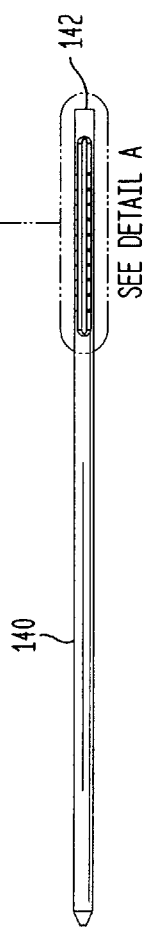
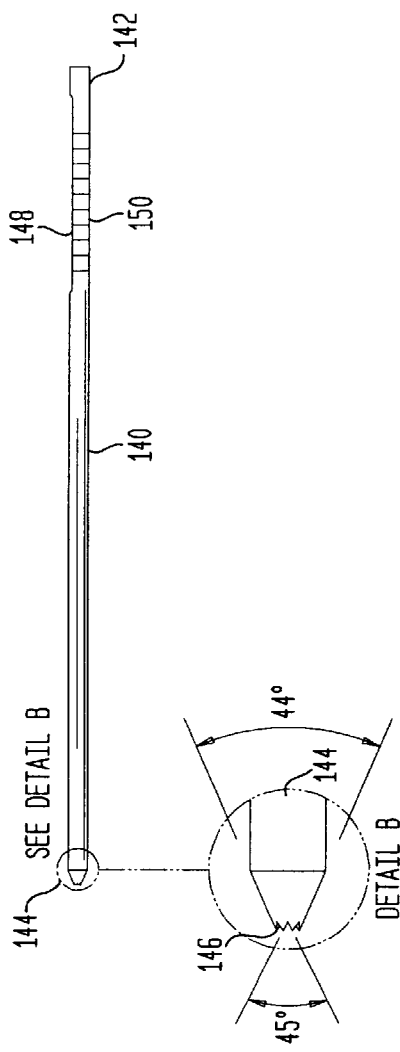
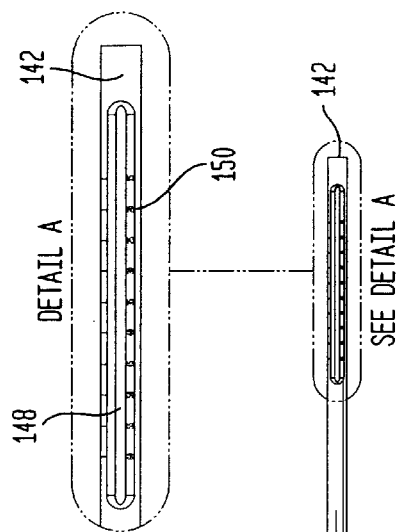
FIG. 7A
FIG. 7B
FIG. 7C

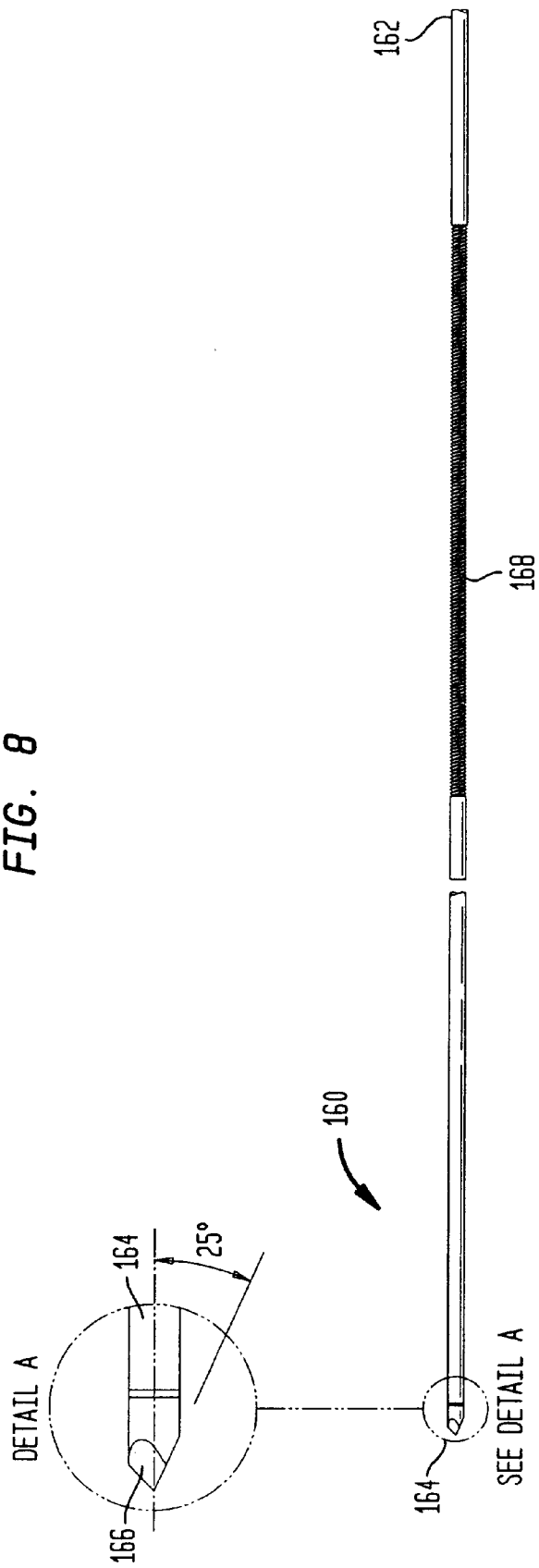

SURGICAL GUIDE SYSTEM FOR STABILIZATION OF THE SPINE

CROSS-REFERENCE TO RELATED APPLICATIONS

Not applicable.

STATEMENT REGARDING FEDERALLY SPONSORED RESEARCH

Not Applicable.

FIELD OF THE INVENTION

The invention relates generally to surgical tools for spinal stabilization, and to methods pertaining thereto. More particularly, this invention relates to a cannulated bone screw system for transfacet and translaminar stabilization of the spine.

BACKGROUND OF THE INVENTION

Thoracolumbar injury is a common pathology of the spine that is responsible for the generation of back or neck pain suffered by many patients. Injury to this area of the spine usually results from a degenerative disc disease, infection or tumor. Treatment of the injury often requires surgical intervention to restore the structural continuity of the spine. The most common surgery for treating such an injury is spinal fusion. Spinal fusion is the surgical joining of one vertebral body to another. This type of treatment often involves internal bracing and instrumentation to stabilize the spine to facilitate the efficient healing of the spine without deformity or instability, while minimizing any immobilization and post-operative care of the patient.

A method suggested by Magerl for treating a thoracic or lumbar pathology involves fixation of successive vertebrae using translaminar screws. Conventionally, these translaminar screws extend through the spinous process and then through the lamina at the facet joint into and through the pedicle of the successively inferior vertebrae. Another current approach utilizes standard fracture fixation techniques typically employed in orthopedic fracture applications. Such fixation techniques can include the use of lag screws to compress bone fragments together. A combination of bone plates and bone screws is also commonly implemented under current fracture fixation techniques. These bone screws and plates provide internal support as the fusion occurs.

With these conventional surgical procedures, screw length is determined by trial and error, probing into the surgical site, or by measurement forceps. Not only are these imprecise and inefficient ways to determine screw length, but result in excess trauma to the injury site and add to the time required to complete the surgery. Further, current systems and methods do not sufficiently enable a surgeon to identify the final screw trajectories to avoid screw collision. There is thus a need for a system and method that provides measurement of appropriate screw length in an easy and reliable manner. There is also a need for improved control over the trajectory of the screw during implantation. Finally, it is desirable to identify appropriate screw insertion sites to ensure that the final screw trajectories will not collide.

SUMMARY OF THE INVENTION

The present invention provides a system of instruments and a method for using these instruments for effective spinal stabilization using cannulated bone screws. In particular, the system and method provide accurate and efficient measurement of the appropriate screw length to be inserted in a patient undergoing spinal stabilization surgery. The system and method offers improved control over the trajectory of the screw during implantation. In addition, the system of the present invention minimizes both the need to use fluoroscopy in conjunction with the implantation process and the visibility problems that exist when installing conventional bone screws in certain patients, e.g., severely obese patients, by enabling accurate orientation or placement of the cannulated bone screws. Moreover, the present invention facilitates proper screw placement by allowing the identification of appropriate screw insertion sites to ensure that the final screw trajectories will not collide.

One method of using the instruments of the present invention involves an improved surgical technique for the placement of cannulated bone screws for use in orthopedic and spinal applications. Specifically, the present method is directed to a surgical technique for the placement of cannulated bone screws for translaminar facet, transfacet, and general orthopedic applications.

The present invention provides a cannulated screw system for effecting the posterior stabilization of the spine. The screw system also acts as an internal fixation device during the time interval required for arthrodesis. The screws can be placed either translaminar or directly through the facets for posterior spine fixation. The bone screws provide internal support as fusion and healing occur.

The system of the present invention includes a guide instrument, an obturator, and a series of cannulae which slide over the obturator and index with the fiducial markings on the obturator to indicate appropriate screw length. In one embodiment of the invention, there is provided an anatomic guide instrument for use with a cannulated guide pin obturator for placement of a guide wire. The anatomic guide references the desired location of the screw tip, and holds and aligns the guide pin obturator. When assembled to the anatomic guide instrument, the obturator references the desired location of the screw head. By placing a surgical cannula over the obturator, measurement marks indicate the length that spans the intended trajectory of the bone screw, which is identified by the distal prong of the guide instrument and the distal end of the obturator.

In addition, the guide instrument incorporates a middle prong which can either reference bony anatomy or provide a visual cue to determine screw trajectory. This orientation can be important for certain applications, e.g., spinal applications, because it establishes a safe trajectory to avoid injury to the surrounding anatomy and nervous tissues. In addition, the use of a guide wire minimizes the risk of damage or fracture of the facet by providing a stable guide for the bone screw with solid bony support.

In another aspect of the present invention, the guide instrument incorporates a multi-position ratchet mechanism which allows the instrument to be manipulated into several geometric configurations, thereby providing the surgeon with an instrument geometry suited to avoid interference with a patient's surrounding soft tissue anatomy.

Further features of the invention, its nature and various advantages, will be more apparent from the accompanying drawings and the following detailed description of the drawings and the preferred embodiments.

BRIEF DESCRIPTION OF THE DRAWINGS

FIG. 7A is a perspective view of an obturator of the present invention;

FIG. 7B is a plan view of the obturator of FIG. 7A, with detailed view of the proximal end;

FIG. 7C is a side view of the obturator of FIGS. 7A and 7B, with detailed view of the distal end;

FIG. 8 is a plan view of the guidewire of FIG. 6, with detailed view of the distal end;

DETAILED DESCRIPTION OF THE INVENTION

The present invention provides a cannulated screw system for posterior stabilization of the spine. The screw system acts as an internal fixation device during the time interval required for arthrodesis. The screws can be placed either translaminar or directly through the facets for posterior spine fixation. The bone screws provide internal support for the vertebrae as fusion and healing occur.

Figure 1:
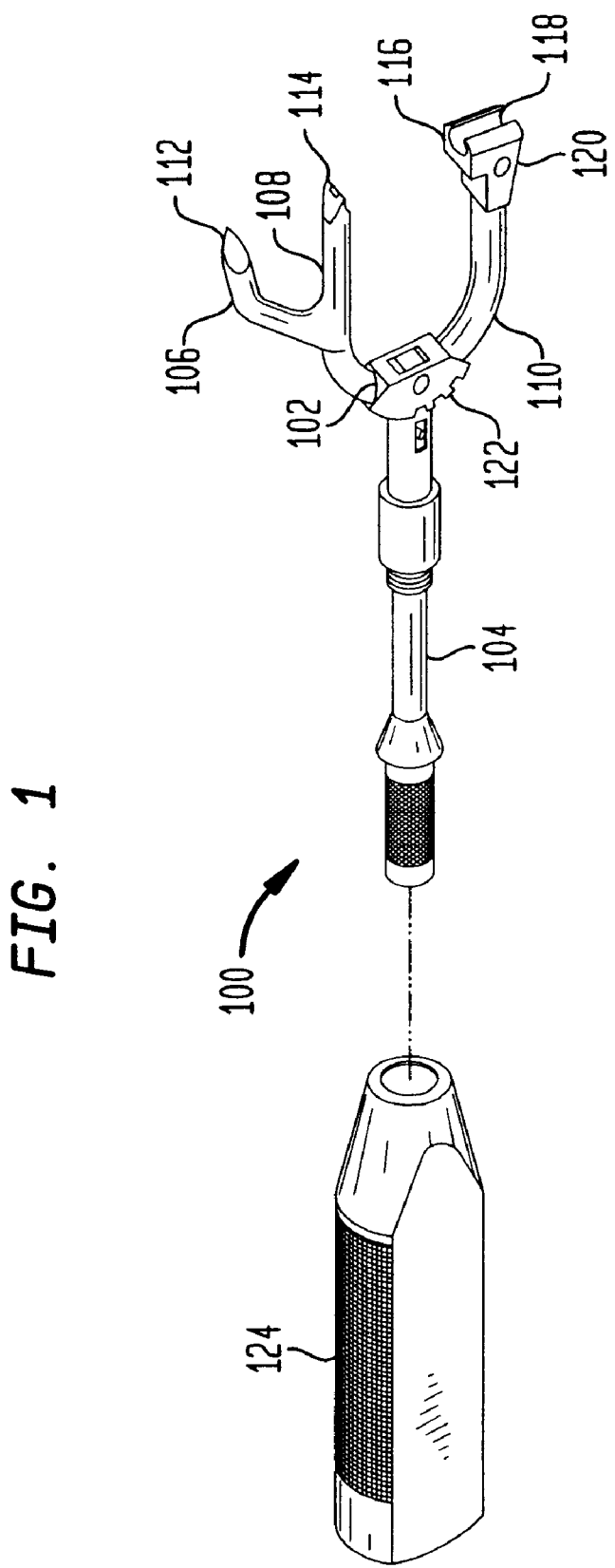
FIG. 1 is an exploded view of an anatomic guide instrument of the present invention.
Figure 2:
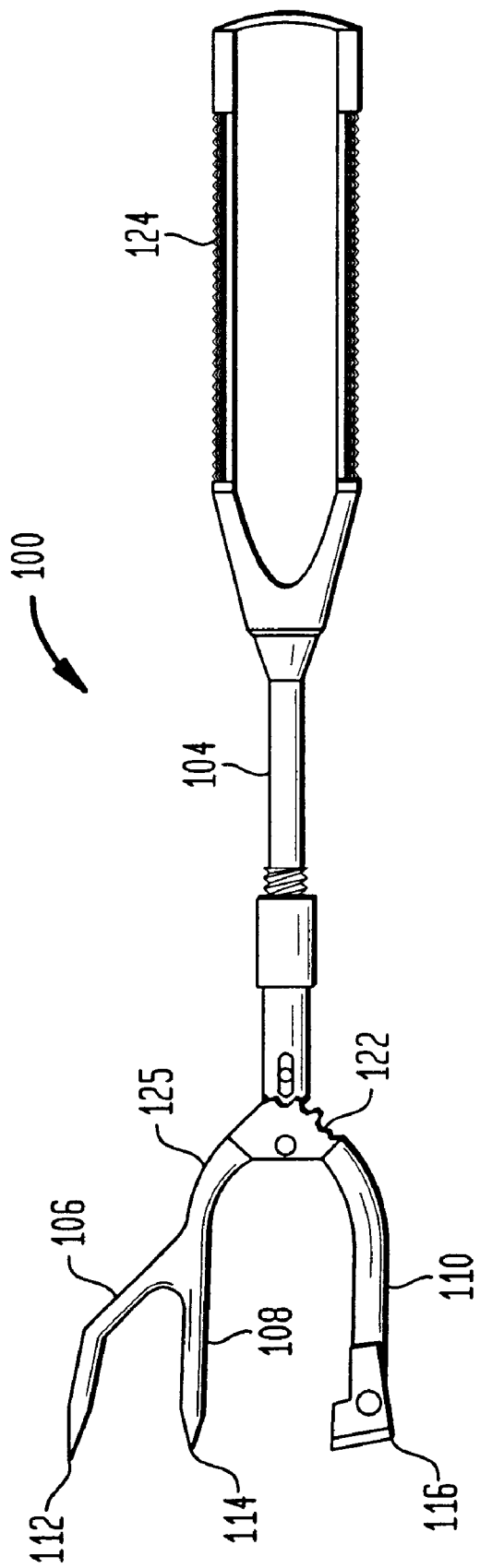
FIG. 2 is a plan view of the anatomic guide instrument of FIG. 1.
Figure 3:
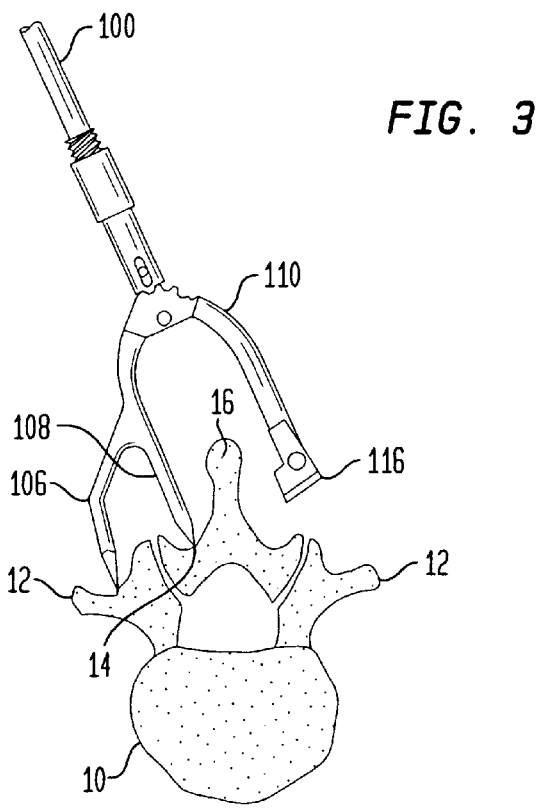
FIG. 3 depicts the anatomic guide instrument of FIG. 2 oriented with respect to a vertebral body.

The system of the present invention includes an anatomic guide instrument 100 as shown in FIGS. 1 and 2. The guide instrument is used to determine and ensure the proper screw trajectory and to help determine the length of a bone screw to be used. The guide instrument 100 comprises a three-prong assembly 102 attached to a shaft 104. As shown in FIG. 1, shaft 104 is detachably connectable to a grip 124. The assembly 102 comprises a distal prong 106, a middle prong 108, and a proximal prong 110. Distal prong 106 is distal-most when properly oriented with respect to a vertebral body 10 during a surgical procedure and has a pointed tip 112 that is adapted to contact the dorsal surface of the base of the transverse process 12, as shown in FIG. 3. Middle prong 108 has a scalloped edge 114 at its distal end that is adapted to register with the dorsal inferior third of the lamina 14. The proximal prong 110 has an obturator block 116 that is intended to be positioned adjacent to the lateral surface of the spinous process 16 contralateral to the facet to be instrumented. Together, the placement of these prongs determines the trajectory and location of the screw itself.

The proximal prong 110 and its obturator block 116 function as a holding block and de facto aiming mechanism for screw insertion. The block 116 includes a locking mechanism 120 for holding and securing elongate instruments therein, and a slot 118 for quick release of the elongate instruments. In one embodiment, the locking mechanism can include a set screw (not shown).

A ratchet connection 122 is formed where the three-prong assembly 102 attaches to shaft 104. The ratchet connection allows the orientation of the three-prong assembly 102 to be changed up to about 60° relative to the shaft 104. Guide instrument 100 is preferably made of surgical grade stainless steel or other corrosive-resistant metals.

Figure 4:
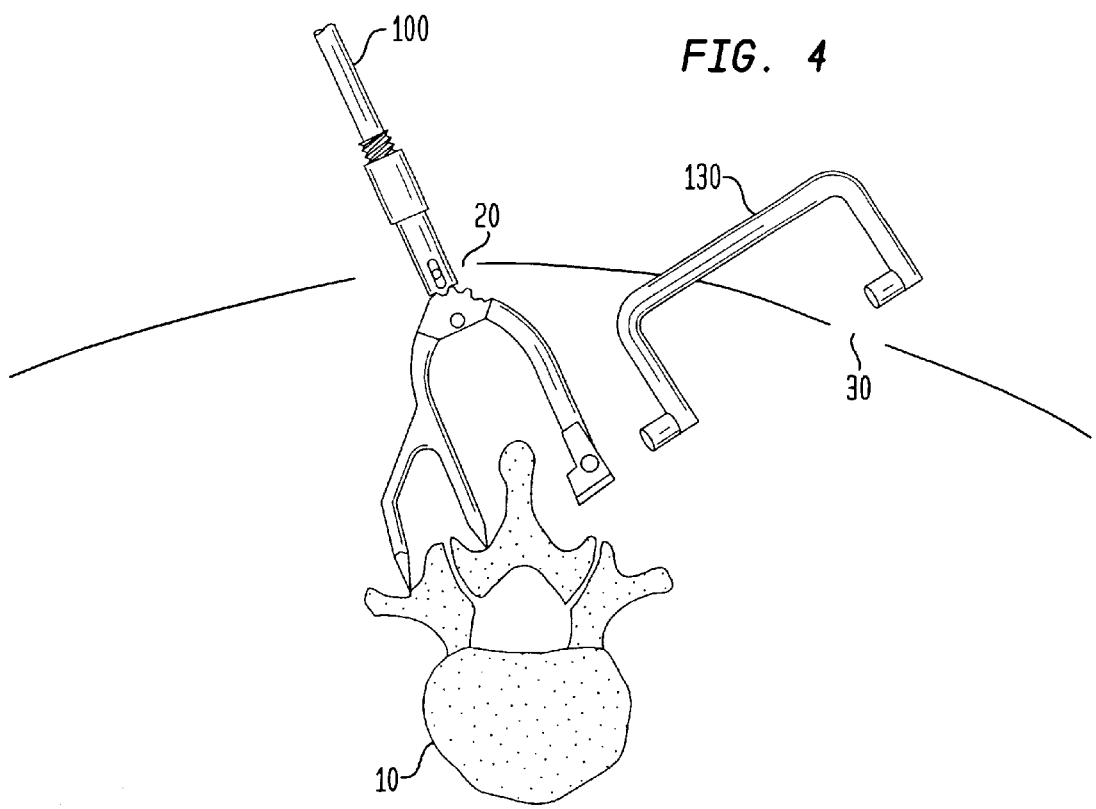
FIG. 4 depicts the anatomic guide instrument of FIG. 2 and a sliding arm instrument of the present invention.
Figure 5:
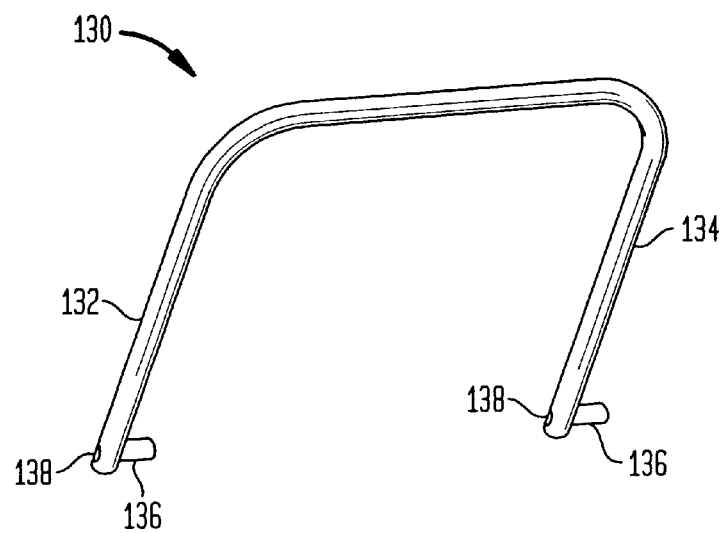
FIG. 5 is a perspective view of the sliding arm instrument of FIG. 4.

To initiate the procedure, a first incision 20 about 5 to 6 inches long is made and then the guide instrument 100 is positioned on the relevant features of the patient's spine 10, as illustrated in FIG. 4. Once the guide instrument 100 is in place, a small, second incision 30 is made lateral to the first incision 20. The location of the second incision 30 can be determined with the aid of a sliding arm instrument 130, shown in FIG. 5, and a guidewire 160, shown in FIG. 8. The sliding arm instrument 130 has a substantially U-shape, with both the proximal arm 132 and distal arm 134 each having a lug 136 extending laterally at an approximately right angle to the arm 132, 134. Lug 136 on the distal arm 134 of the sliding arm instrument 130 is insertable into the obturator block 116 of the anatomic guide instrument 100. Each lug 136 has a channel, or aperture 138 that is aligned with one another. In use, the sliding arm instrument 130 provides a location and alignment mechanism between the second incision 30 and the obturator block 116 of the proximal prong 110 of the guide instrument 100. Together, the guide instrument 100 and the sliding arm instrument 130 enable the surgeon to determine screw trajectory from outside the patient's body.

Figure 6:
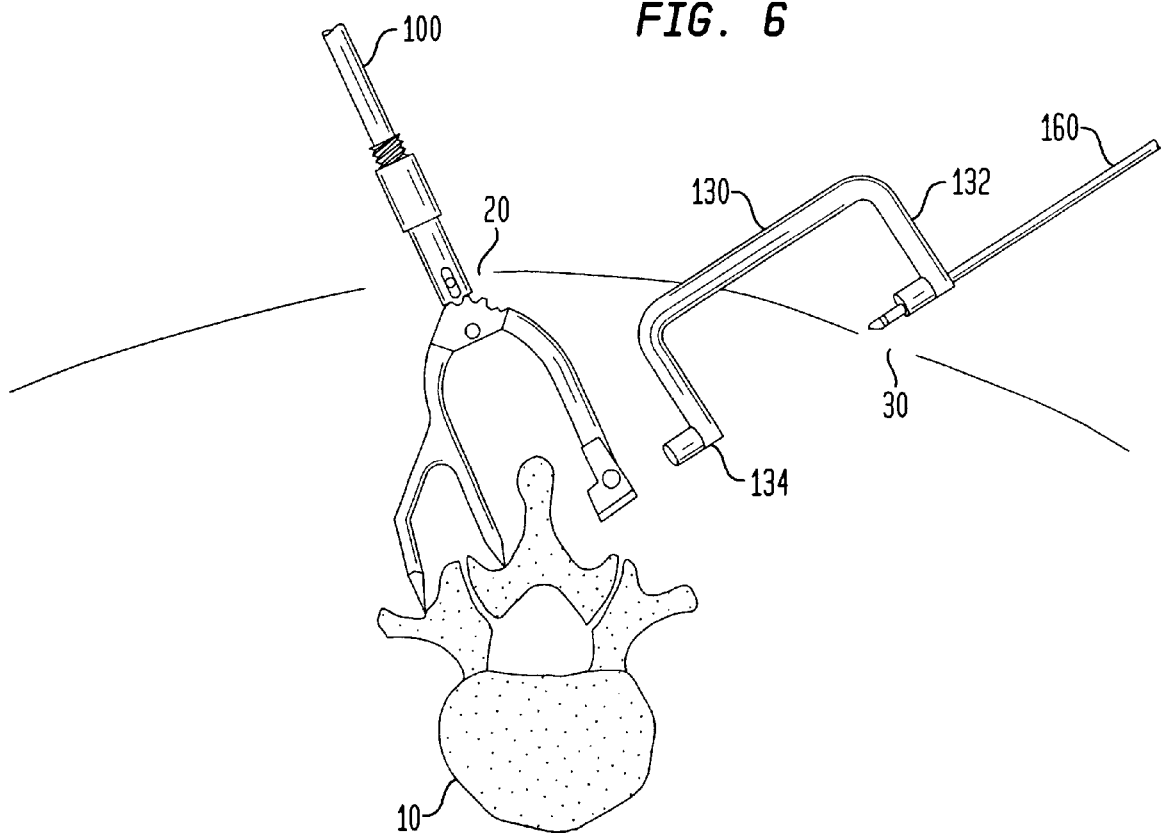
FIG. 6 depicts the anatomic guide instrument, sliding arm instrument, and guidewire of the present invention.

FIG. 6 illustrates how the location of the second incision can be determined. Once the sliding arm instrument 130 is attached to the anatomic guide instrument 100, a guidewire like the one shown in FIG. 8 can be passed through the proximal arm 132 of sliding arm instrument 130. Guidewire 160 has a proximal end 162 and a distal end 164 having a trocar tip 166 that allows the guidewire 160 to be self-drilling. To determine the location of the second incision 30, the guidewire 160 is slid through the lug 136 on the proximal arm 134 until the trocar tip 166 touches the patient's skin, indicating the location of the second incision 30.

After the second incision 30 is made, the sliding arm instrument 130 is removed and a cannulated obturator 140 is passed through the second incision 30 and through the obturator block 116 of the proximal prong 110 of the guide instrument 100 until the distal end of the obturator 140 contacts bone (e.g., the lateral side of the spinous process contralateral to the facet to be instrumented). Obturator 140, as shown in FIGS. 7A to 7C, has a proximal end 142, a tapered distal end 144, and a ridged distal face 146 shown in detail in FIG. 7C to provide traction on the bony surface of the spinous process. The obturator 140 also includes a measurement window 148, representing an opening in the wall of the obturator 140 that aids in determining the desired screw length. As shown in detail in FIG. 7B, marks, or indicia 150 representing screw lengths surround the window 148. Obturator 140 can be inserted so that the distal end 144 extends to the middle prong 108. The obturator 140 can also pass through the scalloped end 114 and extend all the way to the distal prong 110.

Figure 9A:
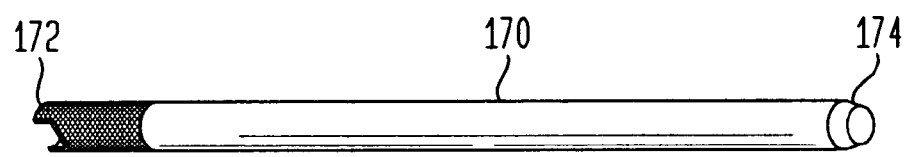
FIG. 9A is a perspective view of a cannula of the present invention.

Once the obturator 140 is in place within the obturator block 116, a first cannula 170 similar to the one shown in FIG. 9A is placed over the obturator 140. The obturator 140 includes calibrated indicia 150 that, with the aid of the first cannula 170, helps the surgeon determine the proper length of the bone screw to be used. The first cannula 170 includes a notched proximal end 172 and a tapered distal end 174 to facilitate tunneling through soft tissue. The desired screw length can be determined by aligning the proximal end 172 of the first cannula 170 with the indicia 150 on the obturator 140. This arrangement enables the proper screw length to be determined by assessing where the proximal end 172 of the cannula 170 registers with marks 150 formed on the obturator 140. This reading approximates the length of the screw as it represents the distance between the distal prong 106 of the guide instrument 100 (the location of the screw tip) and the distal end 144 of the obturator (the location of the screw head). The first cannula 170 can be removed or allowed to remain in place after the screw length is determined.

Next, guidewire 160 is introduced through the obturator 140. The guidewire includes a trocar tip 166 at the distal end 164 that allows it to be self-drilling. Guidewire 160 can extend all the way through obturator 140, through the scalloped edge 114 of middle prong 108 of the guide instrument 100, until the trocar tip 166 rests at the pointed tip 112 of the distal prong 106. The location of the distal prong 106 represents the location of the tip of the screw to be inserted. The axis of guidewire 160 is located approximately 2-3 mm away from the axis that connects the tips of the middle prong 114 and distal prong 112 of guide instrument 100. This offset constrains the screw trajectory to be properly oriented within the center of the lamina of the posterior spine.

Figure 10:
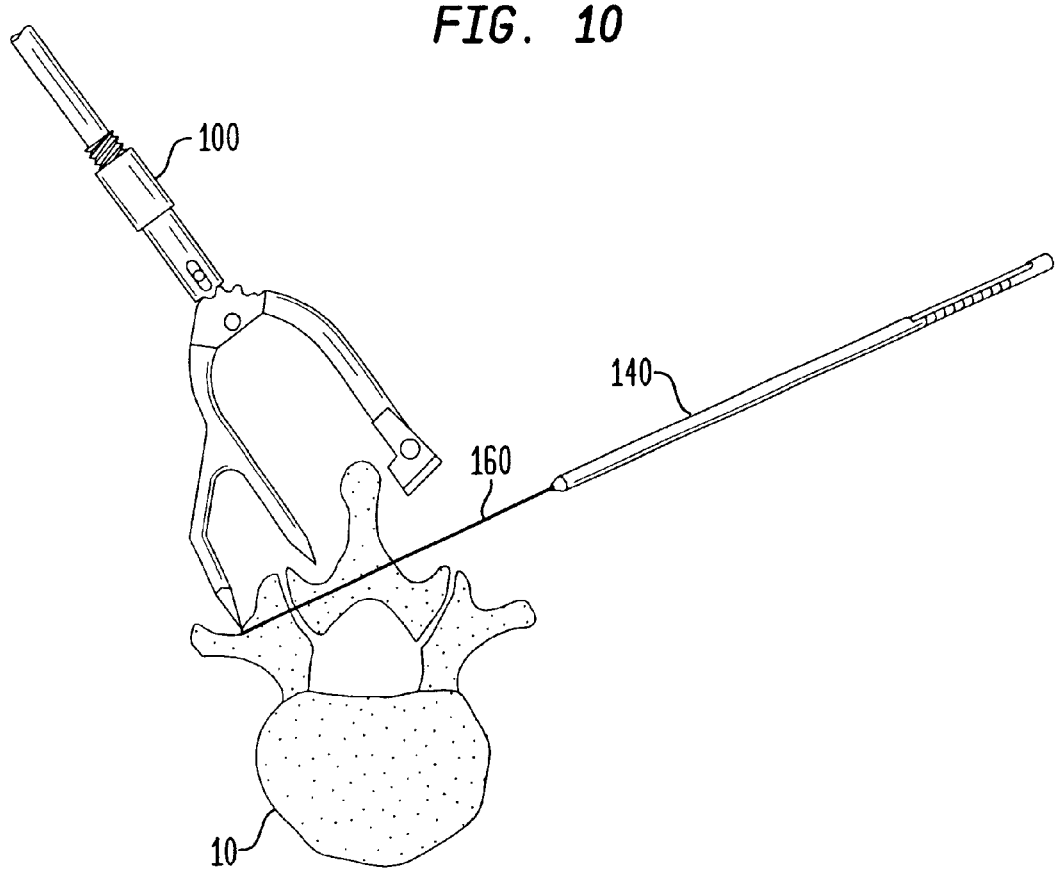
FIG. 10 depicts the removal of the anatomic guide instrument of FIG. 2 from the surgical site.

After guidewire 160 is inserted into obturator 140, the locking mechanism 120 of the guide instrument 100 is unlocked and the obturator 140 is disengaged from the guide instrument 100. Preferably, guide instrument 100 can be removed at this point. To effect removal of the guide instrument 100, the obturator 140 can be slightly retracted towards the surgeon, while guidewire 160 stays in place and the guide instrument 100 is lifted away from the vertebral body, as shown in FIG. 10. Following the introduction of the guidewire 160, the first cannula 170, if previously removed, is repositioned over the obturator 140 until its distal end 174 contacts the guide instrument 100 while the obturator 140 remains in contact with the lateral surface of the spinous process. When first cannula 170 is in position, the obturator 140 can be removed, leaving the guidewire 160 and first cannula 170.

Figure 9B:
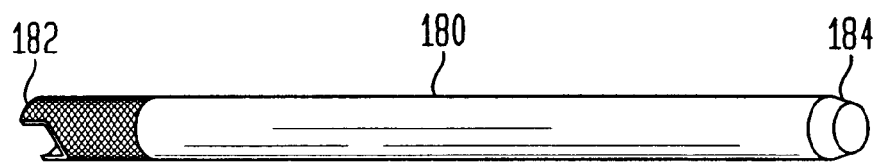
FIG. 9B is a perspective view of another cannula of the present invention.
Figure 9C:
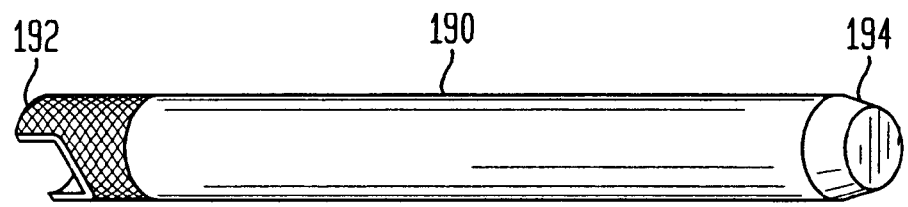
FIG. 9C is a perspective view of yet another cannula of the present invention.
Figure 11:
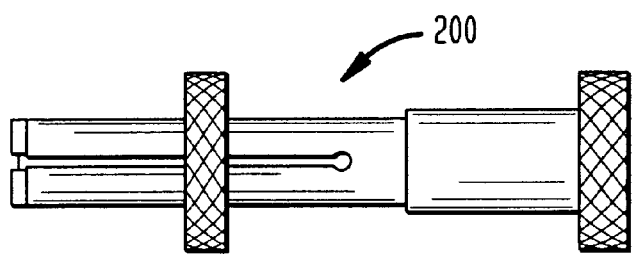
FIG. 11 is a plan view of a drill stop of the present invention.
Figure 12:
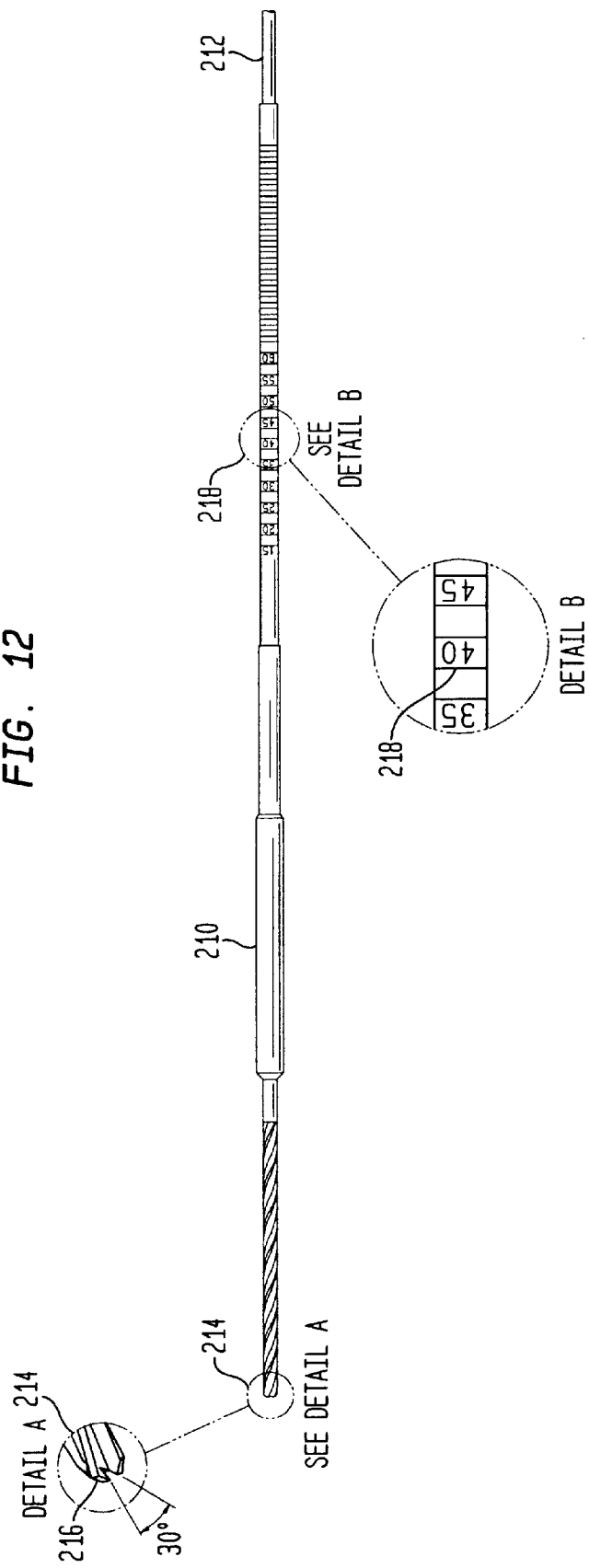
FIG. 12 is a plan view of a drill bit of the present invention, with detailed views.

At this point, a drill stop 200 shown in FIG. 11 is assembled onto a cannulated drill bit 210 as shown in FIG. 12. Cannulated drill bit 210 has proximal end 212 connectable to a surgical drill. Distal end 214 may include specialized cutting flutes 216 as shown in detail in FIG. 12 to facilitate drilling into hard bone. Near proximal end 212 on drill bit 210 are markings 218 shown in detail that correspond to screw lengths. The drill bit 210 is placed over the guidewire 160 and used to drill to the desired depth. The cannulae 170, 180, 190 are sized at an appropriate length to limit drilling depth as determined by adjustment of the drill stop 200 as referenced by indicia 218. The drill bit 210 is then removed and a second cannula 180 shown in FIG. 9B is placed over the first cannula 170 and the first cannula 170 is removed. Second cannula 180 includes a tapered distal end 184 and a notched proximal end 182. Thereafter, a third cannula 190 is placed over the second cannula and the second cannula is removed. Third cannula 190 also includes a tapered distal end 194 and a notched proximal end 192. As clearly shown in FIGS. 9A to 9C, cannulae 170, 180 and 190 are graduated in size. The use of cannulae with progressively larger diameters helps prevent coring of soft tissue by gently displacing tissue to larger open diameters.

Figure 13:
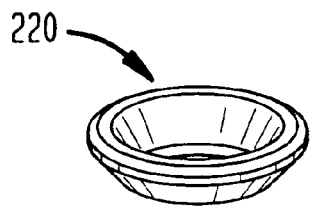
FIG. 13 is a perspective view of a washer of the present invention.

Once the third cannula 190 is in place, an optional washer 220 such as the one shown in FIG. 13 can be inserted over the guidewire 160 and through the cannula 190 to the proper position adjacent the bone 14. Use of a polyaxial washer 220 optimizes the contact area with bone. However, if the washer 220 is not desired, the third cannula 190 need not be used. Next, a screw 230, 240 is inserted over the guidewire 160 and through the cannula 190 and the washer 220 (if present) into the predrilled hole in the vertebral bone 10.

Figure 14:
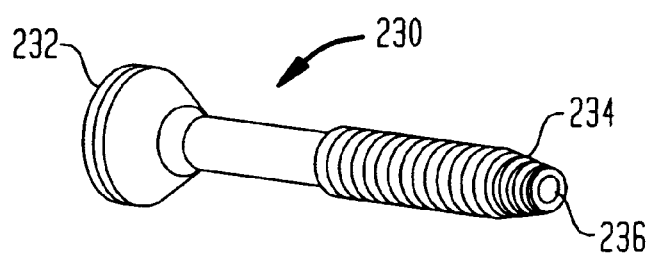
FIG. 14 is a perspective view of a partially threaded cannulated screw of the present invention.
Figure 15:
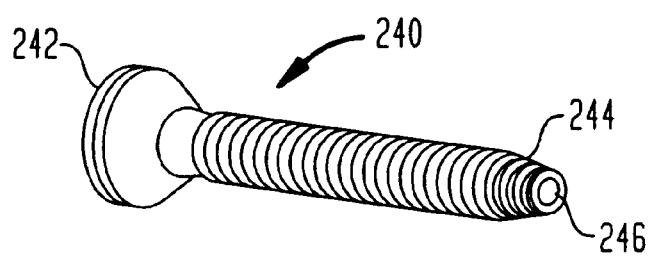
FIG. 15 is a perspective view of a substantially fully threaded cannulated screw of the present invention.

Two types of screws 230, 240 as illustrated in FIGS. 14 and 15 are available in the present system. The first is a substantially fully threaded screw 240, while the second is a partially threaded screw 230 with a non-threaded lag region. The screws 230, 240 are available in sizes between 15 and 60 mm (partially threaded screws 220 are only available in sizes between 25 and 60 mm), thus accommodating a wide anatomical range. Screws 230, 240 are preferably made of a titanium alloy, but could be made of any suitable biocompatible metal or plastic.

In a translaminar-transfacet procedure, a partially-threaded screw 230 as illustrated in FIG. 14 and a substantially fully threaded screw 240 as shown in FIG. 15 are used in combination, to avoid interference. Both are cannulated, to be inserted around guidewire 160. Partially-threaded screw 230 includes head 232, tapered end 234, and through-hole 236. Likewise, substantially fully threaded screw 240 has head 242, tapered end 244, and through-hole 246.

Figure 16A:
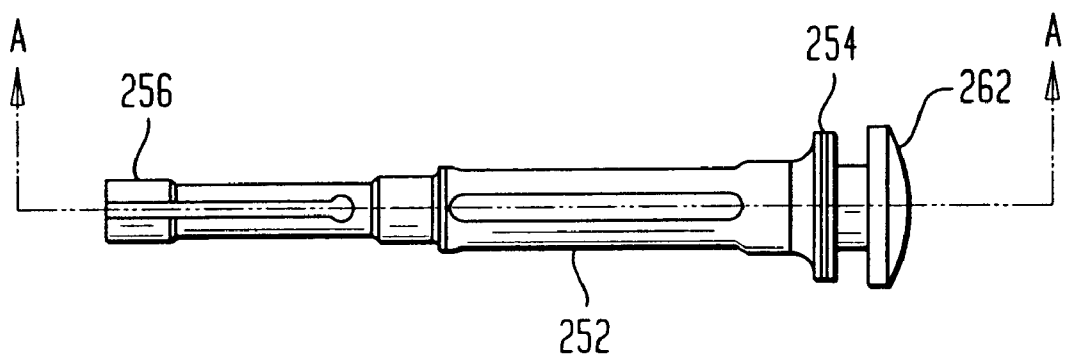
FIG. 16A is a plan view of a screw insertion instrument of the present invention.
Figure 16B:
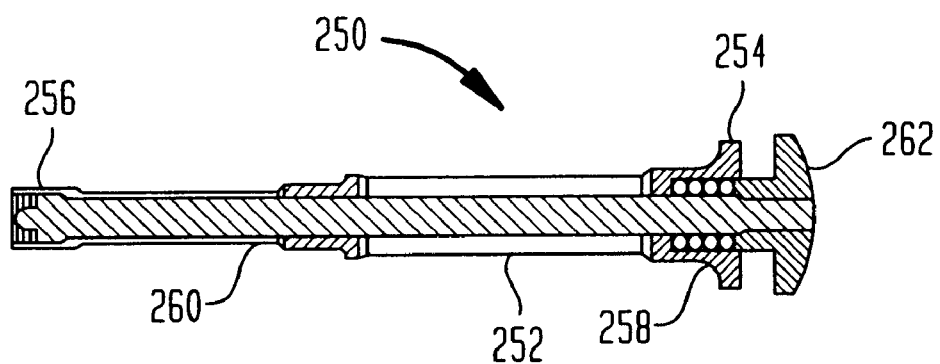
FIG. 16B is a cross-sectional view of the screw insertion instrument of FIG. 16A, along lines A—A.

The screws 230 and 240 can be inserted over guidewire 160 with screw placement instrument 250. As seen in FIGS. 16A and 16B, screw placement instrument 250 includes shaft 252 having a lip 254 at one end. As illustrated in FIG. 16B, within shaft 252 are a spring 254 and a plunger 260 having a receiving end 256 and a head 262. Receiving end 256 clasps the screw 230, 240 until released by depressing head 262 against lip 254 of the screw placement instrument 250.

Figure 17A:
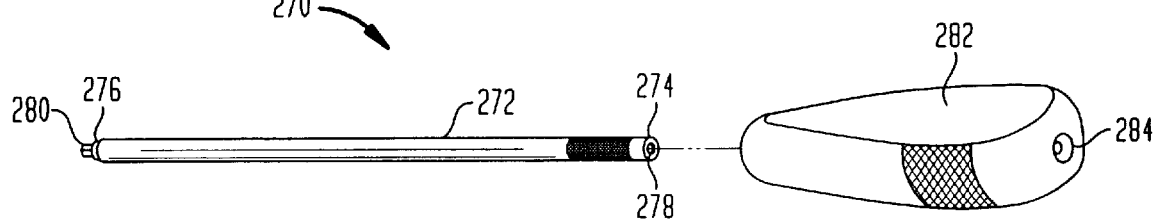
FIG. 17A is an exploded view of a screwdriver of the present invention.
Figure 17B:
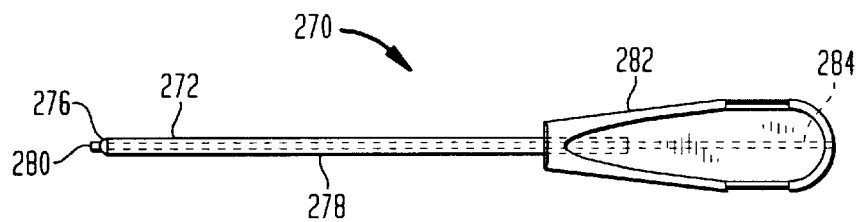
FIG. 17B is a cross-sectional view of the screwdriver of FIG. 17A.

A screwdriver 270 as shown in FIGS. 17A and 17B can be implemented to implant screws 230, 240. Screwdriver 270 includes shaft 272 and a distal end 276 having a hexagonal head 280 attached thereto. The proximal end 274 is coupled to grip 282. Both shaft 272 and grip 282 have through-holes 278, 284 that are aligned, as shown in FIG. 17B. As such, the screwdriver 270 is able slide over guidewire 160 to engage and effect tightening of screws 230, 240. The screw 230, 240 is fully inserted when the distal edge of grip 282 contacts the proximal end 192 of the third cannula 190.

Figure 18A:
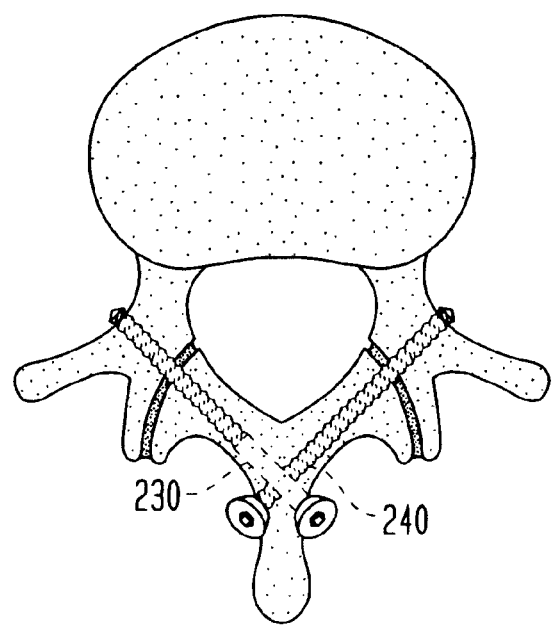
FIG. 18A is a cross-sectional view of the screws of FIGS. 14 and 15 fully inserted.
Figure 18B:
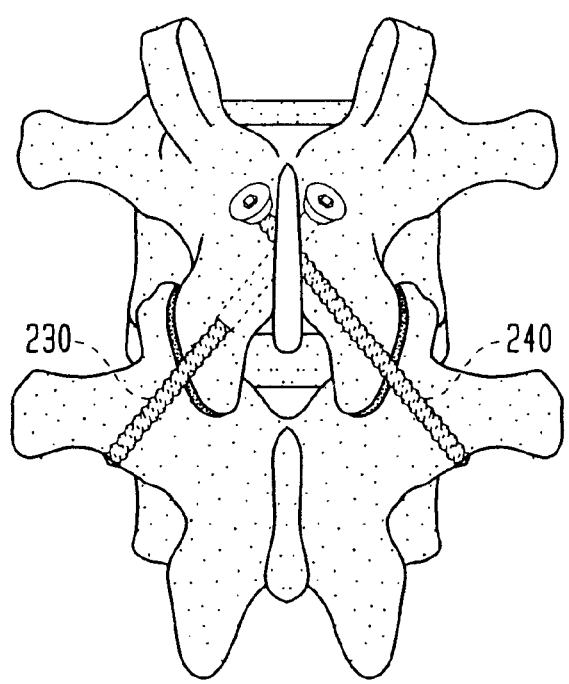
FIG. 18B is another cross-sectional view of the screws of FIGS. 14 and 15 fully inserted.

The screws are inserted through the lateral surfaces of the spinous process, cross within the spinous process, pass through the contralateral lamina and facet joint, and terminate at the entrance to the pedicle. It is recommended that a substantially fully threaded screw 240 and a partially threaded screw 230 be used at each level to minimize screw interference at the region where the screws cross, as shown in FIGS. 18A and 18B. It is critical for appropriate screw insertion sites to be identified to ensure that the final screw trajectories will not collide.

The following outlines suggest exemplary surgical techniques for a translaminar-facet and transfacet procedure using the present invention.

Translaminar-Facet Procedure

1. In preparation for implant placement, prepare the surgical site to provide adequate visualization of the anatomy that includes both facet joints 12, the lamina 14, spinous process 16, and the base of the transverse processes. If desired, carefully remove the joint capsule and joint cartilage from the facet joints and pack with bone graft. Avoid removing subchondral bone.

Adjust the angle of the shaft 104 of the guide assembly 100 as needed to avoid interference with surrounding soft tissue anatomy.

2. Place the distal prong 106 of the guide assembly 100 on the dorsal surface of the base of the transverse process. Register the scalloped end, or notch 114 of the middle prong 108 on the dorsal inferior third of the lamina 14, as shown in FIG. 3. The placement of these prongs defines the trajectory and location of the guidewire 160. The placement of the guidewire 160 then controls screw placement.

3. A secondary incision 30 is used through which the guidewire 160, obturator 140, cannulae 170, 180, 190, washer 220, and screw 230, 240 are passed. The secondary incision 30 is lateral to the primary incision 20. The sliding arm instrument 130 should be used to identify the site of the secondary incision 30 to provide an optimal trajectory for the obturator 140 and cannulae 170, 180, 190 to lead to the site of the primary incision.

4. Insert the lug 136 of the sliding arm instrument 130 into the obturator block 116 of the anatomic guide instrument 100. It is not necessary to engage the set screw 120 on the anatomic guide instrument 100. The opposite (distal) lug 136 is outside of the surgical site, and is automatically aligned with the final trajectory for screw placement. By placing the guidewire 160 through the distal lug 136, the location of a secondary incision site 30 can be identified. Then, a small one centimeter stab wound incision is made at this site. Use a blunt dissection instrument to establish a path between this secondary incision 30 and the primary incision 20. This minimizes disruption to subcutaneous connective tissues and clears space for the obturator 140 and other guide instruments.

5. Introduce the obturator 140 into the anatomic guide instrument 100 and advance the obturator 140 until its tip contacts the lateral surface of the spinous process 16, contralateral to the facet to be instrumented. Insertion is facilitated by rotating the obturator 140 as it is located within obturator block 116. The obturator tip 144 must be dorsal to the intersection of the lamina with the spinous process. This entrance point is a critical point and occasionally the middle prong 108 may move dorsally and will no longer contact the lamina.

However, the distal prong 106 must remain on the dorsal surface of the base of the transverse process 12. Tighten the set screw 120 on the anatomic guide instrument 100 to lock the obturator 140 in place.

6. Place the first cannula 170 over the obturator 140. Make sure that the cannula 170 contacts the anatomic guide instrument 100 at the obturator block 116 and that the obturator 140 contacts the lateral surface of the spinous process 12 when reading the screw length measurement. The desired screw length can be determined where the end 172 of the cannula registers with the index marks 150 on the obturator 140. This distance is a measure of the length between the distal prong 106 of the anatomic guide instrument 100 (located at the screw tip 234, 244) and the obturator tip 144 (located at the screw head 232, 242).

If it is desired to engage additional screw length beyond the location of the distal prong 106 of the anatomic guide instrument 100, add the incremental length to that measured using the cannula 170 and obturator 140.

7. Remove the first cannula 170 by sliding it back over the obturator 140.

8. Insert the guidewire 160 through the obturator 140. Advance the guidewire 160 until the black marking 168 on the guidewire 160 registers with the index mark 150 on the obturator 140 that corresponds with the desired screw length.

9. Disengage the obturator 140 from the anatomic guide instrument 100 by unlocking the set screw 120 on the anatomic guide instrument 100. Slide the obturator 140 back until it is completely disengaged from the guide instrument 100. Remove the anatomic guide instrument 100 while leaving the obturator 140 and guidewire 160 in place (the slot 118 on the obturator block 116 of the anatomic guide instrument 100 allows for disassembly from guidewire 160). Slide the obturator 140 back down over the guidewire 160 to once again contact the spinous process 12.

10. Reinsert first cannula 170 over the obturator 140.

11. Remove the obturator 140.

12. Assemble the cannulated drill stop 200 onto the cannulated drill. Set the drill stop 200 on the drill bit 210 to the desired screw length. The index markings 218 on the drill bit 210 indicate drilling depth. Note: The drill stop 200 is firmly locked when the floating ring is engaged over the collet to lock the drill stop 200 to the drill bit 210. Failure to appreciate this step could result in overdrilling.

Because this is a cannulated system, use a cannulated drill system.

13. Place the drill bit 210 over the guidewire 160 and through the first cannula 170. Drill until the drill stop 200 contacts the end of the cannula 172.

14. Remove the drill. Occasionally the guidewire 160 will come out with the drill. If so reinsert the guidewire 160 into the hole in preparation for cannulated screw insertion. Slide the second cannula 180 over the first cannula 170. Remove the first cannula 170, leaving the second cannula 180 in place. In a similar manner, replace the second cannula 180 with the third cannula 190.

Graduating the cannulae 170, 180, 190 in this manner will help prevent maceration or "coring" of soft tissues as progressively larger cannulae are inserted. At times, the guidewire 160 may loosen when the drill is removed. In that case, reinsert the guidewire 160 into the previously-drilled hole.

15. Insert the washer 220 over the guidewire 160. Pick the desired screw 230, 240 from the screw tray using the screw placement instrument 250 and slide the screw 230, 240 over the guidewire 160. Then, slide the screwdriver 270 over the guidewire 160, engage the hex opening of the screw head, and insert the screw 230, 240. The screw 230, 240 is fully inserted when the handle 282 of the screwdriver 270 contacts the 192 end of the cannula. Be careful not to advance the guidewire 160 with the drill 210.
16. Remove the guidewire 160. It is recommended that screw placement be verified in coronal and sagittal planes with x-ray or fluoroscopy.
17. Repeat steps 1–14 to place a second screw 230, 240 on the opposite side of the spinous process 12. Choose the entry site of the second screw carefully so as to avoid any interference with the first screw. In general, the entrance site should be a minimum of 5 mm cephalad of the centerline of the first screw. It is recommended that the second screw be a fully threaded screw 240.
18. Close in standard fashion.

Transfacet Procedure

1. In preparation for implant placement, smooth and clear surface of bony prominences to optimize visualization of the anatomy. Adjust the angle of the shaft 104 on the guide instrument 100 to promote clear access to the surgical site.
2. Place the distal prong 106 of the guide instrument 100 on the base of the transverse process 12 at the junction of the superior facet.
3. Determine the screw entry point so that the facet joint can be instrumented. Assemble the obturator 140 into the guide instrument 100 with the tip of the obturator 140 contacting the facet at the determined entry point. Tighten the set screw 120 to lock the obturator 140 in place.
4. Place the first cannula 170 over the obturator 140. The position of the end 172 of the cannula 170, relative to the depth index marks 150 on the obturator 140, indicates screw length to the distal prong 106 from the entrance point on the facet as determined in step 3.
5. Remove the first cannula 170.
6. Place the guidewire 160 through the obturator 140.
7. Insert the guidewire 160 through the obturator 140. Advance the guidewire 160 until the guidewire 160 indexes with the desired screw length as indicated on the obturator 140.
8. Unlock the set screw 120, leaving the obturator 140 on the guidewire 160 but disengage the guidewire 160 from the anatomic guide instrument 100.
9. Remove the anatomic guide instrument 100, leaving the guidewire 160 and obturator 140 in place. Slide the obturator 140 over the guidewire 160 to the surface of the facet.
10. Reinsert the first cannula 170 over the obturator 140.
11. Remove the obturator 140.
12. Assemble the drill. Set the drill stop 200 at the desired screw engagement depth. The drill stop 200 is firmly locked when the floating ring is moved over the expanding collet to the desired drill depth, as marked on the drill bit 210.
13. Drill through the first cannula 170 until the drill stop 200 makes contact with the distal end of 174 the cannula 170. Be careful not to advance the guidewire 160 with the drill.
14. The screw 230, 240 and washer 220 can be inserted through the third cannula 190. Use the following sequence:
    a. Remove the drill and slide the second cannula 180 over first cannula 170.
    b. Next, replace the first cannula 170 with the second cannula 180.
    c. Replace the second cannula 180 with the third cannula 190.
    d. Graduating the cannulae in this manner will help protect soft tissues by preventing "coring".
    e. Remove the first and second cannulae 170, 180.
15. Insert the washer 220 over the guidewire 160 (optional). Select the desired screw 230, 240 and slide it over the engaged guidewire 160. Next slide the screwdriver 270 over the guidewire 160 and engage the hex of the screw. Insert the screw.

The screw 230, 240 is fully inserted when the handle 282 of the screwdriver 270 contacts the distal end 194 of the cannula 190. Do not allow the guidewire 160 to be advanced unintentionally with either the drill or screws.
16. Remove the guidewire 160. Verify screw placement with x-ray or fluoroscopy is desired.
17. Repeat on opposite side.
18. Close in standard fashion.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A system for determining screw length and screw trajectory of a screw for insertion into a vertebral body, comprising:
    an anatomic guide instrument adapted to be placed against the vertebral body where the screw is to be inserted, the guide instrument having a shaft with a three-prong assembly formed at a distal end thereof, the assembly comprising a first prong, second prong, and third prong, the third prong including a holding block;
    a cannulated obturator insertable through the holding block, the obturator having a window and markings indicative of optimal screw length; and
    a cannula for placement over the cannulated obturator;
    wherein the obturator and cannula together are effective to indicate screw length.

2. The system of claim 1, wherein the first and second prongs are adapted to be placed against the vertebral body, while the third prong is adapted to define the trajectory of the screw to be inserted.

3. The system of claim 1, wherein the second prong includes a scalloped edge at a distal-most end.

4. The system of claim 1, wherein the first prong includes a pointed tip at a distal-most end.

5. The system of claim 1, wherein the holding block further includes a locking mechanism.

6. The system of claim 5, wherein the locking mechanism comprises a set screw.

7. The system of claim 1, further including a sliding arm instrument for insertion into the holding block, the sliding arm instrument being substantially U-shaped and having a distal arm and a proximal arm, each arm having a lug extending therefrom, wherein each lug includes an aperture for guiding the obturator into the holding block from outside the patient's body.

8. The system of claim 7, further including a guidewire for inserting through the lugs of the sliding arm instrument and the obturator.

9. The system of claim 8, wherein the guidewire includes a trocar tip at a distal-most end.

10. The system of claim 8, wherein the cannula is one of a set of cannulae adapted to be sequentially placed over the guidewire for gently displacing tissue around the vertebral body.

11. The system of claim 1, wherein the shaft pivots with respect to the three-prong assembly.

12. The system of claim 11, wherein the shaft pivots by a ratcheting mechanism.

13. The system of claim 11, wherein the shaft pivots up to about 60° with respect to the three-prong assembly.

14. An anatomic guide instrument for determining screw length and screw trajectory of a screw for insertion into a vertebral body, comprising:
   a handle connected to a shaft with a three-prong assembly formed at a distal end thereof, the assembly comprising a first prong, second prong, and third prong including a holding block, the shaft being angularly adjustable with respect to the three-prong assembly;
   wherein the first and second prongs are adapted to be placed against the vertebral body where the screw is to be inserted, while the third prong is adapted to define the trajectory of the screw.

15. The instrument of claim 14, wherein the second prong includes a scalloped edge at a distal-most end.

16. The instrument of claim 14, wherein the first prong includes a pointed tip at a distal-most end.

17. The instrument of claim 14, wherein the holding block further includes a locking mechanism.

18. The instrument of claim 17, wherein the locking mechanism comprises a set screw.

19. The instrument of claim 14, wherein the shaft pivots with respect to the three-prong assembly.

20. The instrument of claim 19, wherein the shaft pivots by a ratcheting mechanism.

21. The instrument of claim 19, wherein the shaft pivots up to about 60° with respect to the three-prong assembly.

22. A method for determining screw length and screw trajectory of a screw for insertion into a vertebral body, comprising:
   providing an anatomic guide instrument adapted to be placed against the vertebral body where the screw is to be inserted, the guide instrument having a handle with a three-prong assembly formed at a distal end thereof, the assembly comprising a first prong, second prong, and third prong, the third prong including a holding block;
   placing the anatomic guide instrument through the first incision and against the vertebral body such that the first prong and second prong contact an aspect of the vertebral body;
   inserting a cannulated obturator through the holding block, the obturator having a window and markings indicative of optimal screw length;
   placing a cannula having a proximal end and a distal end over the cannulated obturator; and
   determining the optimal screw length by reading where the distal end of the cannula aligns with the markings of the cannulated obturator.

23. The method of claim 22, further including the step of inserting a sliding arm instrument into the holding block, the sliding arm instrument being substantially U-shaped and having a distal arm and a proximal arm, each arm having a lug extending therefrom wherein each lug includes an aperture formed therein.

24. The method of claim 23, further including the step of identifying a site for a secondary incision, comprising inserting a guidewire through the aperture of the proximal arm of the sliding arm instrument until a distal-most end of the guidewire contacts the patient's skin.

25. The method of claim 24, further including the steps of introducing through the secondary incision a set of cannulae, a screwdriver, a washer, and screws to the primary surgical site.

26. The method of claim 25, wherein the step of introducing the set of cannulae comprises sequentially placing each cannula over the guidewire for gently displacing tissue around the vertebral body.

* * * * *